United States Patent
Schlueter et al.

(10) Patent No.: US 7,847,046 B2
(45) Date of Patent: Dec. 7, 2010

(54) OPHTHALMIC AND OTORHINOLARYNGOLOGICAL DEVICE MATERIALS CONTAINING PHENYLENE-SILOXANE MACROMERS

(75) Inventors: Douglas C. Schlueter, Azle, TX (US); David L. Jinkerson, Benbrook, TX (US)

(73) Assignee: Alcon, Inc., Hunenberg (CH)

( * ) Notice: Subject to any disclaimer, the term of this patent is extended or adjusted under 35 U.S.C. 154(b) by 457 days.

(21) Appl. No.: 12/111,270

(22) Filed: Apr. 29, 2008

(65) Prior Publication Data

US 2008/0269418 A1    Oct. 30, 2008

Related U.S. Application Data

(60) Provisional application No. 60/914,968, filed on Apr. 30, 2007.

(51) Int. Cl.
*C08G 77/20* (2006.01)
(52) U.S. Cl. ............... 526/279; 528/32; 351/160 H
(58) Field of Classification Search .......... 528/32; 526/279; 351/160 H
See application file for complete search history.

(56) References Cited

U.S. PATENT DOCUMENTS

| | | | | |
|---|---|---|---|---|
| 4,563,514 A * | 1/1986 | Liu et al. | | 427/515 |
| 5,346,980 A * | 9/1994 | Babu | | 528/40 |
| 5,578,380 A * | 11/1996 | Babu | | 428/447 |
| 6,723,816 B2 | 4/2004 | Salamone et al. | | 528/32 |
| 6,730,767 B2 | 5/2004 | Salamone et al. | | 528/43 |
| 6,762,271 B2 | 7/2004 | Salamone et al. | | 528/43 |
| 6,777,522 B2 | 8/2004 | Lai et al. | | 528/43 |
| 6,784,259 B2 * | 8/2004 | Keller et al. | | 525/477 |
| 6,951,914 B2 | 10/2005 | Lai et al. | | 528/43 |
| 6,972,034 B2 | 12/2005 | Tran et al. | | 623/6.41 |
| 7,009,024 B2 | 3/2006 | Salamone et al. | | 528/43 |
| 7,060,297 B2 | 6/2006 | Karakelle et al. | | 424/488 |
| 7,064,173 B2 | 6/2006 | Rubinsztajn et al. | | 528/14 |
| 2005/0033001 A1 | 2/2005 | Cella et al. | | 528/16 |
| 2006/0281888 A1 | 12/2006 | Schlueter | | 526/318.44 |
| 2006/0282163 A1 | 12/2006 | Schlueter et al. | | 623/6.11 |

FOREIGN PATENT DOCUMENTS

WO    WO2006/138188    12/2006
WO    WO2006130402    12/2006

OTHER PUBLICATIONS

Li et al., "Asymmetric synthesis of Optically Active Poly(silyl ether)s Having Reactive Si-H Groups by Stereoselective Cross-Dehydrocoupling Polymerization of Bis(silane)s with Diols," *Macromolecules*, vol. 33, pp. 5311-5314 (2000).
Li et al., "Efficient Synthesis of Poly(silyl ether)s by Pd/C and RhCl(PPh$_3$)$_3$ Catalyzed Cross-Dehydrocoupling Polymerization of Bis(hydrosilane)s with Diols" *Macromolecules*, vol. 32. pp. 6871-6873 (1999).
Li et al., "Synthesis and Properties of Polymers Containing Silphenylene Moiety via Catalytic Cross-Dehydrocoupling Polymerization of 1,4-Bis(dimethylsilyl)benzene," *Macromolecules*, vol. 32, pp. 8768-8773 (1999).
Rubinsztajn et al., "A new polycondensation process for the preparation of polysiloxane copolymers," *Macromolecules*, vol. 38, pp. 1061-1063 (2005).
Rubinsztajn et al., "Formation of siloxane bonds via new condensation process," *Polymer Preprints*, vol. 45(1), pp. 635-636 (2004).
Zhang et al., "Dehydrocoupling Polymerization of Bis-silanes and Disilanols to Poly(Silphenylenesiloxane) as Catalyzed by Rhodium Complexes," *Macromolecules*, vol. 33, pp. 3508-3510 (2000).
Zhou et al., "Tris(pentafluoropheynl)borane as a Superior Catalyst in the synthesis of Optically Active SiO-Containing Polymers," *Macromolecules*, vol. 38, pp. 6902-6908 (2005).

* cited by examiner

*Primary Examiner*—Margaret G Moore
(74) *Attorney, Agent, or Firm*—Patrick M. Ryan

(57) ABSTRACT

Disclosed are soft, high refractive index, acrylic device materials having improved strength. The materials contain a phenylene-siloxane macromer.

17 Claims, No Drawings

OPHTHALMIC AND OTORHINOLARYNGOLOGICAL DEVICE MATERIALS CONTAINING PHENYLENE-SILOXANE MACROMERS

This application claims priority to U.S. Provisional Application, U.S. Ser. No. 60/914,968 filed Apr. 30, 2007.

FIELD OF THE INVENTION

This invention is directed to improved ophthalmic and otorhinolaryngological device materials. In particular, this invention relates to soft, high refractive index acrylic device materials that have improved flexibility and strength.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Conventional silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than conventional silicone materials.

U.S. Pat. No. 5,290,892 discloses high refractive index, acrylic materials suitable for use as an intraocular lens ("IOL") material. These acrylic materials contain, as principal components, two aryl acrylic monomers. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable, high refractive index ophthalmic lens materials containing at least about 90 wt. % of only two principal components: one aryl acrylic hydrophobic monomer and one hydrophilic monomer. The aryl acrylic hydrophobic monomer has the formula

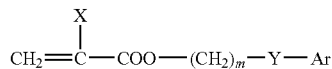

wherein: X is H or $CH_3$;

m is 0-6;

Y is nothing, O, S, or NR, wherein R is H, $CH_3$, $C_nH_{2n+1}$ (n=1-10), iso-$OC_3H_7$, $C_6H_5$, or $CH_2C_6H_5$; and Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

The lens materials described in the '095 Patent preferably have a glass-transition temperature ("Tg") between about −20 and +25° C.

Flexible intraocular lenses may be folded and inserted through a small incision. In general, a softer material may be deformed to a greater extent so that it can be inserted through an increasingly smaller incision. Soft acrylic or methacrylic materials typically do not have an appropriate combination of strength, flexibility and non-tacky surface properties to permit IOLs to be inserted through an incision as small as that required for silicone IOLs. The mechanical properties of silicone elastomers are improved by addition of an inorganic filler, typically surface treated silica. Surface treated silica improves the mechanical properties of soft acrylic rubbers, too, but reduces the optical clarity of the finished product. Alternative filler materials having a refractive index closer to soft acrylic rubber are needed.

The addition of reinforcing fillers to soft polymers is known to improve tensile strength and tear resistance. Reinforcement stiffens the polymer and improves its toughness by restricting the local freedom of movement of polymer chains, and strengthens the structure by introducing a network of weak fix points. The reinforcing ability of a particular filler depends upon its characteristics (e.g. size and surface chemistry), the type of elastomer with which it is used, and the amount of filler present. Conventional fillers include carbon black and silicate fillers, where the particle size (for maximum surface area) and wettability (for strength of cohesion) are of primary importance. Covalent chemical bonding between the matrix and the filler is generally not required for effective reinforcement. For a review see: Boonstra, "Role of particulate fillers in elastomer reinforcement: a review" *Polymer* 1979, 20, 691, and Gu, et al., "Preparation of high strength and optically transparent silicone rubber" *Eur. Polym. J.* 1998, 34, 1727.

SUMMARY OF THE INVENTION

Improved soft, foldable acrylic device materials which are particularly suited for use as IOLs, but which are also useful as other ophthalmic or otorhinolaryngological devices, such as contact lenses, keratoprostheses, corneal rings or inlays, otological ventilation tubes and nasal implants, have been discovered. These polymeric materials contain phenylene-siloxane macromers.

DETAILED DESCRIPTION OF THE INVENTION

Unless indicated otherwise, all component amounts are presented on a % (w/w) basis ("wt. %").

The device materials of the present invention are copolymers comprising a) a monofunctional acrylate or methacrylate monomer [1], b) a difunctional acrylate or methacrylate cross-linker [2], and c) a phenylene-siloxane macromer [3a] or [3b].

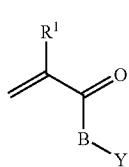

[1]

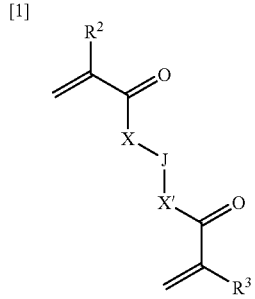

[2]

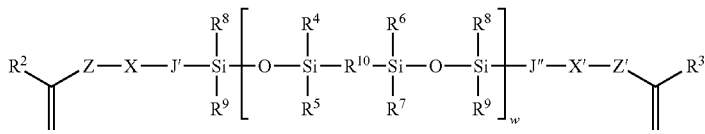

[3a]

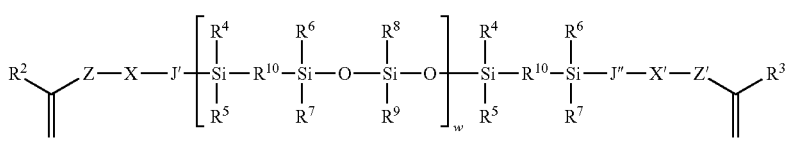

[3b]

wherein:
B=$O(CH_2)_n$, $NH(CH_2)_n$, or $NCH_3(CH_2)_n$;
$R^1$, $R^2$, $R^3$ independently =H, $CH_3$, $CH_2CH_3$, or $CH_2OH$;
X, X' independently =$O(CH_2)_n$, $NH(CH_2)_n$, $NCH_3(CH_2)_n$, $O(CH_2)_nC_6H_4$, $O(CH_2CH_2O)_nCH_2$, $O(CH_2CH_2CH_2O)_nCH_2$, $O(CH_2CH_2CH_2CH_2O)_nCH_2$, or nothing;
J=$(CH_2)_a$, $O(CH_2CH_2O)_b$, O, or nothing, provided that if X and X'=nothing, then J≠nothing;
J', J" independently=$(CH_2)_a$ or nothing, provided that if X and X'=nothing, then J', J"≠nothing;
n=0-12;
Y=$C_6H_5$, $(CH_2)_mH$, or $O(CH_2)_mC_6H_5$;
Z, Z' independently =C(=O) or $OCH_2C_6H_4$;
m=0-12;
a=1-12;
b=1-24;
$R^4$, $R^5$, $R^6$, $R^7$, $R^8$, $R^9$ independently =$(CH_2)_bH$, CH=$CH_2$, CH=$C(CH_3)$, $CH_2CH$=$CH_2$, $CH_2CH$=$CHCH_3$, $CH(CH_3)_2$, $CH_2CH(CH_3)_2$, $O(CH_2)_mC_6H_5$, $O(CH_2)_mC_6H_4(OH)C(O)C_6H_5$, $CH_2CH_2CH_2NH_2$, $CH_2CH_2CH_2NHCH_3$, $CH_2CH_2CH_2N(CH_3)_2$, $CH_2CH_2CH_2NHCH_2CH_2NH_2$, $CH_2CH(CH_3)CH_2NHCH_2CH_2NH_2$, $(CH_2)_aOC(O)C(R^1)$=$CH_2$, $(CH_2)_bSH$, $CH_2CH_2CH_2OCH_2(O)CH_2$, $CH(CH_3)NHCH_2CH_3$, $CH(CH_3)N(CH_3)CH_2CH_3$, $CH(CH_3)N(CH_2CH_3)_2$, cyclopentyl, cyclohexyl, $CH_2CH_2CN$, $CH_2CH_2CH_2CN$, $CH_2CH_2CH(CH_3)CN$, $CH_2Cl$, $CH_2CH_2Cl$, $CH_2CH_2CH_2Cl$, $CH_2CH_2C_6H_4CH_2Cl$, $CH_2Si(CH_3)_3$, $CH_2Si(CH_2CH_3)_3$, $CH_2CH_2CF_3$, $CH_2NCO$, $CH_2NHC_6H_5$, $C_6F_5$, phenyl, or naphthyl, each optionally substituted with $C_1$-$C_{12}$ alkyl, $C_1$-$C_{12}$ alkoxy, $C_1$-$C_{12}$ cycloalkyl, $C_1$-$C_{12}$ cycloalkoxy, $NO_2$, OH, CN, NCO, $NH_2$, F, Br, Cl, I, or $(CH_2CH_2O)_bH$;

$R^{10}$=phenyl, biphenyl, diphenylether, or naphthyl, each optionally substituted with $C_1$-$C_{12}$ alkyl, $C_1$-$C_{12}$ alkoxy, $C_1$-$C_{12}$ cycloalkyl, $C_1$-$C_{12}$ cycloalkoxy, $NO_2$, OH, CN, NCO, $NH_2$, F, Br, Cl, I, or $(CH_2CH_2O)_bH$; and
w=3-120.

Preferred monomers of formula [1] are those wherein:
B=$O(CH_2)_n$;
$R^1$=H or $CH_3$;
n=1-4; and
Y=$C_6H_5$.

Preferred monomers of formula [2] are those wherein:
$R^2$, $R^3$ independently =H or $CH_3$;
X, X' independently =$O(CH_2)_n$, $O(CH_2)_nC_6H_4$, or nothing;
J=$O(CH_2CH_2O)_b$ or nothing, provided that if X and X'=nothing, then J≠nothing;
n=0-6; and
b=1-24.

Preferred macromers of formulas [3a] and [3b] are those wherein:
$R^2$, $R^3$ independently =H or $CH_3$;
$R^4$, $R^5$, $R^6$, $R^7$ independently =$CH_3$ or $CH_2CH_3$;
$R^8$, $R^9$ independently =$CH_3$, phenyl, or naphthyl;
$R^{10}$=phenyl, biphenyl, or naphthyl;
X, X'=$O(CH_2)_n$, $O(CH_2CH_2O)_nCH_2$, $O(CH_2CH_2CH_2O)_nCH_2$, $O(CH_2CH_2CH_2CH_2O)_nCH_2$, or nothing;
J', J"=$(CH_2)_a$;
a=3-12;
Z, Z'=C(=O); and
w=3-90.

Most preferred macromers of formulas [3a] and [3b] are those of formulas [4a] and [4b]:

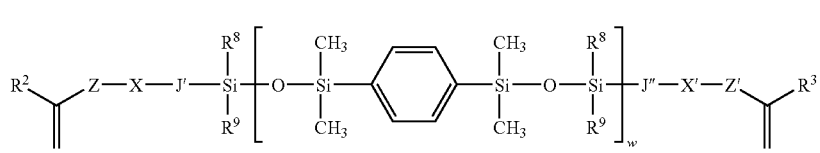

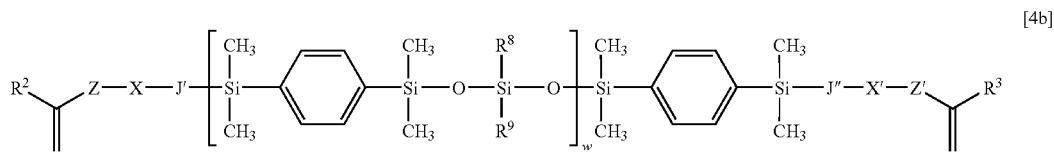

wherein
R² R³ independently =H or CH₃;
R⁸, R⁹ independently =CH₃ or phenyl;
J', J"=(CH₂)ₐ;
a=3;
X, X'=O(CH₂)ₙ;
n=0;
Z, Z'=C(=O); and
w=10-70.

Monomers of formula [1] are known and can be made by known methods. See, for example, U.S. Pat. Nos. 5,331,073 and 5,290,892. Many monomers of formula [1] are commercially available from a variety of sources.

Monomers of formula [2] are known and can be made by known methods, and are commercially available. Preferred monomers of formula [2] include ethylene glycol dimethacrylate ("EGDMA"); diethylene glycol dimethacrylate; 1,6-hexanediol dimethacrylate; 1,4-butanediol dimethacrylate; poly(ethylene oxide)dimethacrylate (number average molecular weight 200-1000); and their corresponding acrylates.

Macromers of formula [3] can be made by known methods. For example, one method for synthesizing the phenylene-siloxane portion of macromer [3] involves the polymerization reaction of 1,4-bis(dimethylsilyl)-benzene (DMSB) with diphenyldimethoxysilane using a tris(pentafluorophenyl)borane catalyst (Scheme 1). This polymerization provided a polymer of $M_w$ 29,940 in a 1:1 stiochoimetry and $M_w$ 4,060 in a 1.1:1 stoichiometry.

Scheme 1. Polycondensation of 1,4-Bis(dimethylsilyl)benzene with diphenyldimethoxysilane

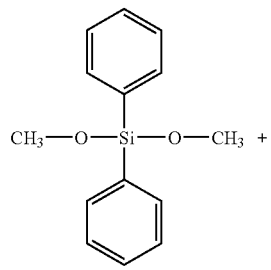

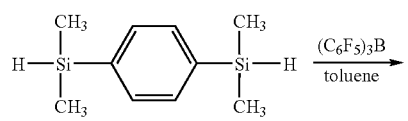

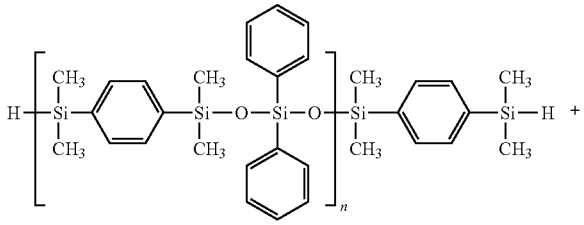

CH₄

References for Scheme 1:
Rubinsztajn, et al., *Polymer Preprints* 2004, 45(1), 635.
Rubinsztajn, et al., *Macromolecules* 2005, 38, 1061-63.
Cella, et al., U.S. patent application Ser. No. 10/918,608, published Feb. 10, 2005.
From the literature, the Tg for the polymer of Scheme 1 was reported to be −3.3° C. (Y. Li and Y. Kawakami, *Macromolecules* 1999, 32, 8768-8773) or −7.7° C. (see ref. b. above).

Another method for synthesizing the phenylene-siloxane portion of macromer [3] relies on the dehydrocoupling reaction of either DMSB or phenylmethylsilane with 1,4-bis(hydroxydimethylsilyl)benzene using Wilkinson's catalyst [(Ph₃P)₃RhCl] (Scheme 2).

Scheme 2. Dehydrocoupling Polymerization to Prepare Poly(Phenylene-siloxane)

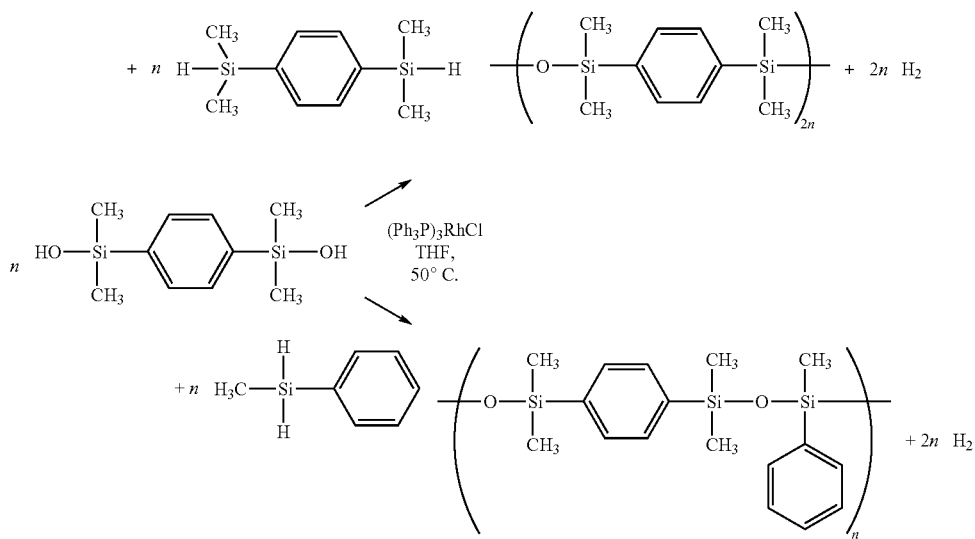

Reference for Scheme 2:

R. Zhang, J. E. Mark, A. R. Pinhas *Macromolecules* 2000, 33, 3508-10.

Literature reports polymers from upper reaction in Scheme 2 with Mn of 8.5-17K (reference. see Zhang and Mark listed above)

For the polymer in the lower reaction of Scheme 2, the $T_g$ was reported to be −35.5° C., but for the polymer in the upper reaction it was −19° C. (Li, Y.; Kawakami, Y. *Macromolecules* 1999, 32, 8768-73).

Acrylate or methacrylate groups can be added to the ends of phenylene-siloxanes using, for example, the method shown in Scheme 3.

Scheme 3. Reaction sequence leading to methacrylate-functionalized poly(phenylene-siloxane) macromonomer

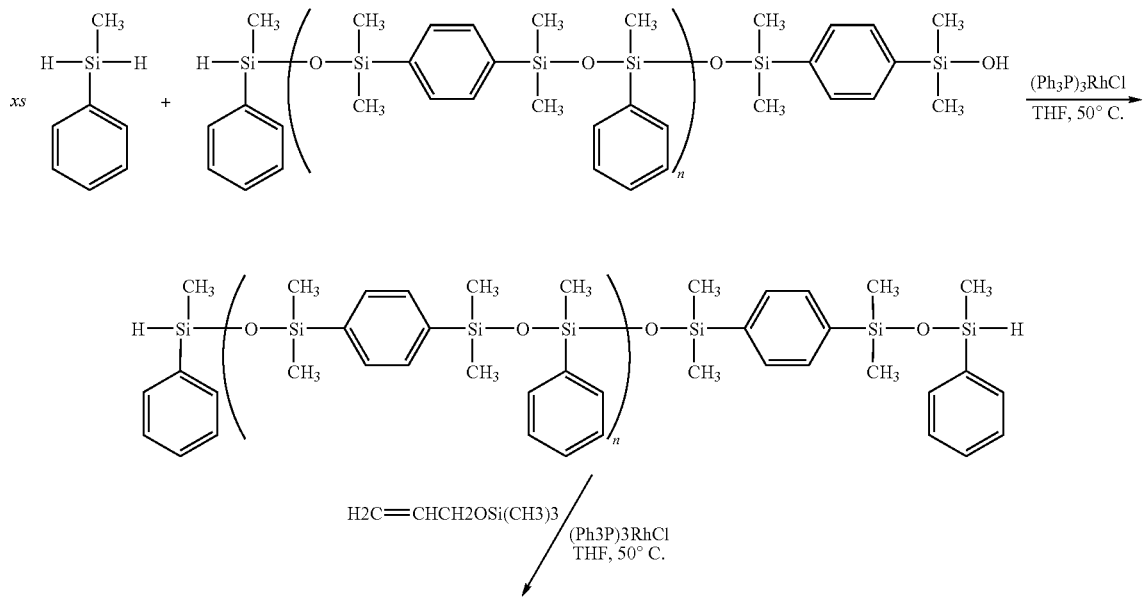

-continued

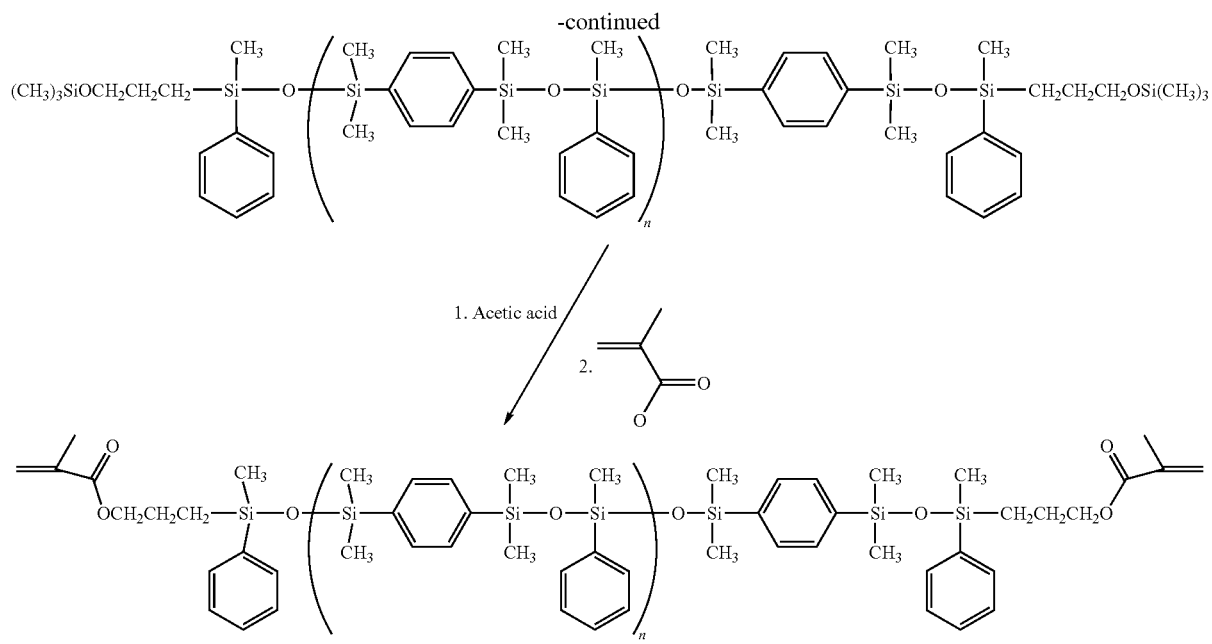

The copolymeric materials of the present invention contain monomer [1] in an amount from 45 to 85%, preferably from 45 to 75%. The difunctional cross-linker [2] concentration can be on the order of 10 to 15% of the total concentration when X and X'=nothing and J=O(CH$_2$CH$_2$O)$_b$, where b>5, and preferably less than about 3% for lower molecular weight difunctional cross-linkers, for example when X, X'=OCH$_2$ and J=(CH$_2$)$_2$.

The materials of the present invention have at least one macromer of [3]. The total amount of macromer [3] depends on the desired physical properties for the device materials. The copolymeric materials of the present invention contain a total of at least 1% and can contain as much as 95% of macromer [3]. Preferably, the copolymeric device materials will contain 5-70% of macromer [3]. Most preferably, the device materials will contain 10-50% of macromer [3].

The copolymeric device material of the present invention optionally contains one or more ingredients selected from the group consisting of a polymerizable UV absorber and a polymerizable colorant. Preferably, the device material of the present invention contains no other ingredients besides the monomers of formulas [1] and [2], the macromer [3], and polymerizable UV absorbers and colorants.

The device material of the present invention optionally contains reactive UV absorbers or reactive colorants. Many reactive UV absorbers are known. A preferred reactive UV absorber is 2-(2'-hydroxy-3'-methallyl-5'-methylphenyl)benzotriazole, commercially available as o-Methallyl Tinuvin P ("oMTP") from Polysciences, Inc., Warrington, Pa. UV absorbers are typically present in an amount from about 0.1-5%. Suitable reactive blue-light absorbing compounds include those described in U.S. Pat. No. 5,470,932. Blue-light absorbers are typically present in an amount from about 0.01-0.5%. When used to make IOLs, the device materials of the present invention preferably contain both a reactive UV absorber and a reactive colorant.

In order to form the device material of the present invention, the chosen ingredients [1], [2], and [3] are combined and polymerized using a radical initiator to initiate polymerization by the action of either heat or radiation. The device material is preferably polymerized in de-gassed polypropylene molds under nitrogen or in glass molds.

Suitable polymerization initiators include thermal initiators and photoinitiators. Preferred thermal initiators include peroxy free-radical initiators, such as t-butyl (peroxy-2-ethyl) hexanoate and di-(tert-butylcyclohexyl) peroxydicarbonate (commercially available as Perkadox® 16 from Akzo Chemicals Inc., Chicago, Ill.). Particularly in cases where the materials of the present invention do not contain a blue-light absorbing chromophore, preferred photoinitiators include benzoylphosphine oxide initiators, such as 2,4,6-trimethylbenzoyldiphenyl-phosphine oxide, commercially available as Lucirin® TPO from BASF Corporation (Charlotte, N.C.). Initiators are typically present in an amount equal to about 5% or less of the total formulation weight, and more preferably less than 2% of the total formulation. As is customary for purposes of calculating component amounts, the initiator weight is not included in the formulation weight % calculation.

The particular combination of the ingredients described above and the identity and amount of any additional components are determined by the desired properties of the finished device material. In a preferred embodiment, the device materials of the present invention are used to make IOLs having an optic diameter of 5.5 or 6 mm that are designed to be compressed or stretched and inserted through surgical incision sizes of 2 mm or less.

The device material preferably has a refractive index in the dry state of at least about 1.47, and more preferably at least about 1.50, as measured by an Abbe' refractometer at 589 nm (Na light source) and 25° C. Optics made from materials having a refractive index lower than 1.47 are necessarily thicker than optics of the same power which are made from materials having a higher refractive index. As such, IOL optics made from materials with comparable mechanical properties and a refractive index lower than about 1.47 generally require relatively larger incisions for IOL implantation.

IOLs constructed of the device materials of the present invention can be of any design capable of being stretched or compressed into a small cross section that can fit through a 2-mm incision. For example, the IOLs can be of what is known as a one-piece or multi-piece design, and comprise optic and haptic components. The optic is that portion which serves as the lens and the haptics are attached to the optic and are like arms that hold the optic in its proper place in the eye. The optic and haptic(s) can be of the same or different material. A multi-piece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use as other ophthalmic or otorhinolaryngological devices such as contact lenses, keratoprostheses, corneal inlays or rings, otological ventilation tubes and nasal implants.

The invention will be further illustrated by the following examples, which are intended to be illustrative, but not limiting.

EXAMPLE 1

Preparation of Poly(diphenylsilloxy-1-dimethylsilyl-4-dimethylsiloxyphenylene)

(a) Chain End Functionalized Phenylene Siloxane Copolymers

The synthesis of a phenylene siloxane copolymer is shown in Reaction 1. A Lewis acid catalyzed polycondensation reaction between diphenyldimethoxysilane [5] and 1,4-bis(dimethylsilyl)benzene [6] yields an alternating copolymer where the end groups are controlled through reaction stoichiometry or end-capping reactions. This polymerization is adapted from a recent literature report and patent application, where Cella et al. teach the use of (pentafluorophenyl)boron as a polycondensation catalyst to prepare polysiloxane copolymers.

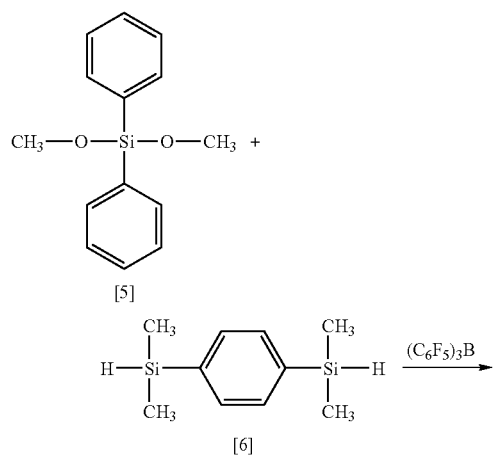

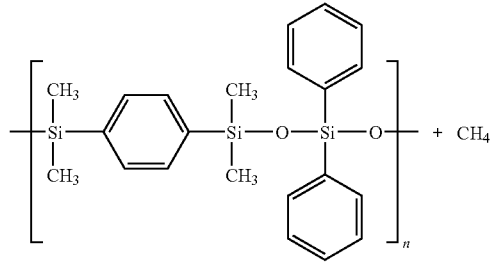

Reaction 1. Synthesis of Phenylene Siloxane Copolymer by Polycondensation Reaction.

To create a chain end functional polymer, the copolymerization is conducted in the presence of a slight excess of one of the monomer components. For example, using a slight excess of 1,4-bis(dimethylsilyl)benzene [6] results in a silane end-capped copolymer [7] (Reaction 2). Likewise, an excess of diphenyldimethoxysilane comonomer will result in a methoxy terminated copolymer.

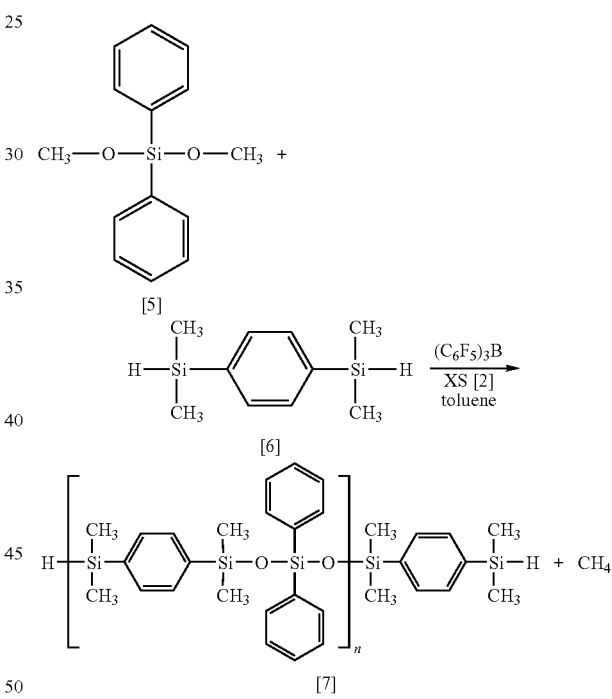

Reaction 2. Synthesis of Silane End-Functional Phenylene Siloxane Copolymer [7] by Polycondensation Reaction in the Presence of Slight Excess of 1,4-bis(dimethylsilyl)benzene [6].

The functionalized copolymers may be combined with multifunctional cross-linkers, for example, mixing [7] with a multifunctional olefin and platinum catalyst, will yield a cross-linked copolymer, that when copolymerized in a suitable lens mold will produce a flexible intraocular lens. Desirable mechanical properties are tuned by changing the copolymer molecular weight, cross-linker concentration and cross-linker functionality.

Alternatively, olefin chain ends may be produced by terminating the polycondensation reaction with an olefin functional silane (Reaction 3).

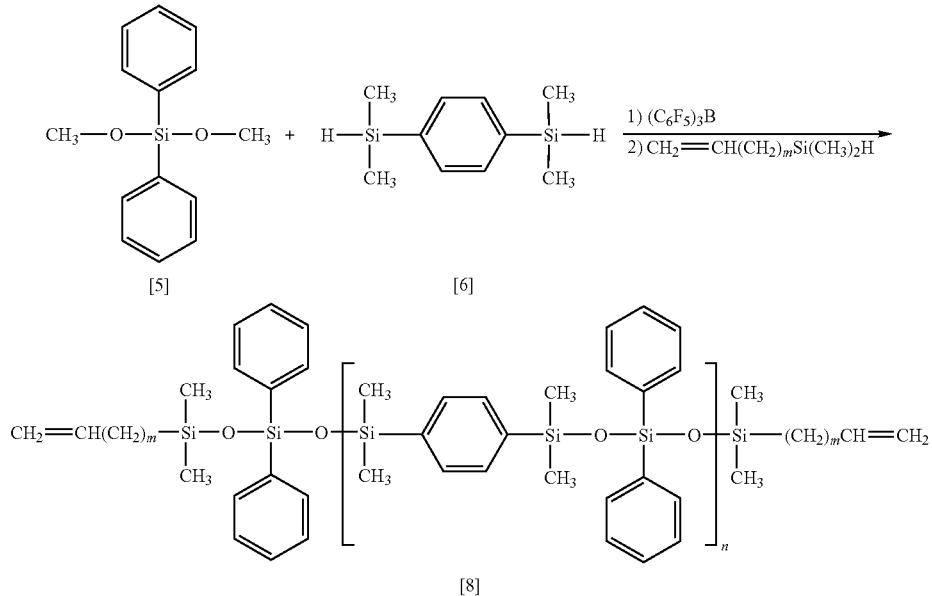

Reaction 3. Synthesis of Olefin End-Functional Phenylene Siloxane Copolymer [8] by Terminating the Polycondensation Reaction with Vinyl Functional Silane.

The subject phenylene siloxanes may also be synthesized using a dehydrocoupling polycondensation reaction, relying on, for example, the dehydrocoupling reaction of either DMSB or phenylmethylsilane with 1,4-bis(hydroxydimethylsilyl)benzene using Wilkinson's catalyst [(Ph$_3$P)$_3$RhCl.

(b) Phenylene Siloxane Copolymer Functionalization: Dimethacrylate-Terminated Phenylene Siloxane Macromonomer Preferably, the difunctional phenylene siloxane are converted to acrylate or methacrylate functionality to allow free radical copolymerization with acrylate and methacrylate monomers.

The terminal silane groups in poly(phenylene siloxane) [7] are converted to hydroxyl groups through hydrosilylation reaction with allyloxytrimethylsilane, followed by deprotection with TBAF or CF$_3$CO$_2$H (Reaction 4). Esterification or the resulting hydroxyl groups with methacryloyl chloride will yield a methacrylate terminated phenylene siloxane copolymer [6]. The end-functionalized siloxane copolymer is then mixed with a monofunctional methacrylate or acrylate monomer and a free radical initiator and polymerized in a suitable lens mold to form a transparent flexible intraocular lens. Optionally a multifunctional acrylic or methacrylic cross-linker, for example ethylene glycol dimethacrylate or 1,4-butanediol diacrylate, can be added to adjust the mechanical properties.

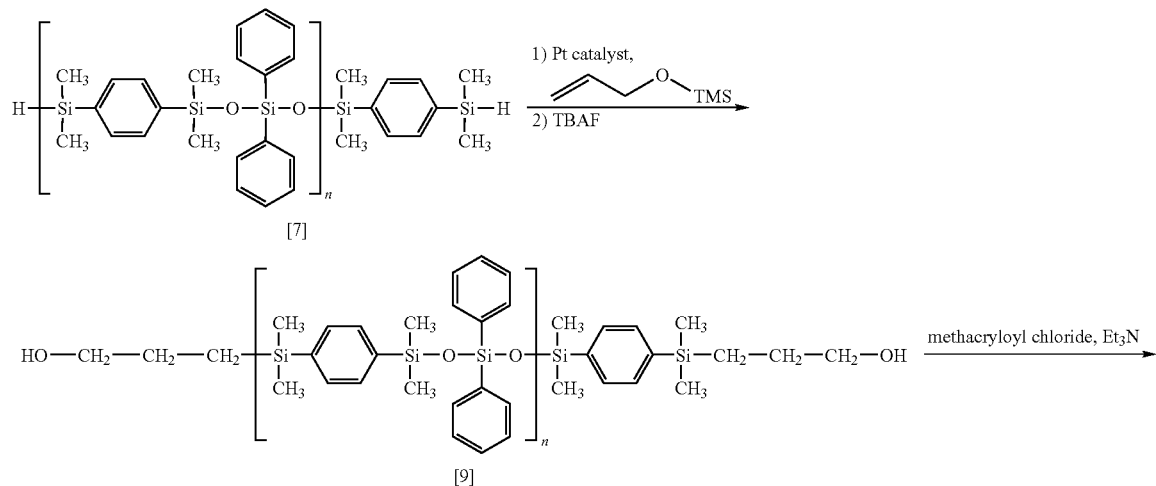

-continued

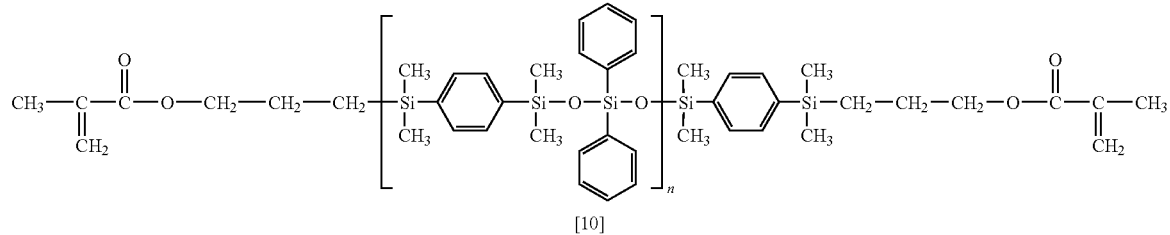

[10]

Reaction 4. Synthesis of Dimethacrylate Terminated Phenylene Siloxane Copolymer [10].

Alternatively the olefin terminated phenylene siloxane [8] can be converted to a hydroxyl terminated copolymer by hydroboration (Reaction 5). Following oxidative work-up the hydroxyl terminated polymer is treated with methacryloyl or acryloyl chloride in the presence of triethylamine to produce a methacrylate or acrylate functional macromonomer [12].

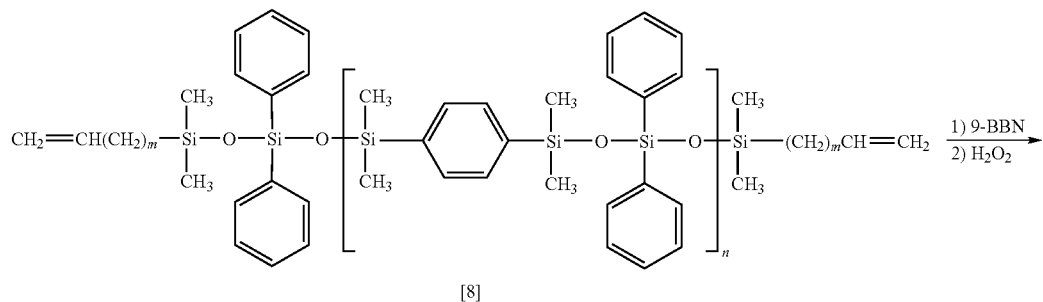

[8]

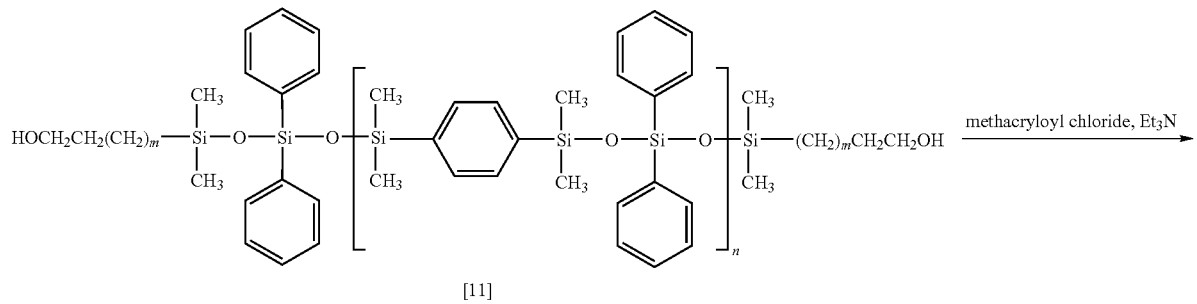

[11]

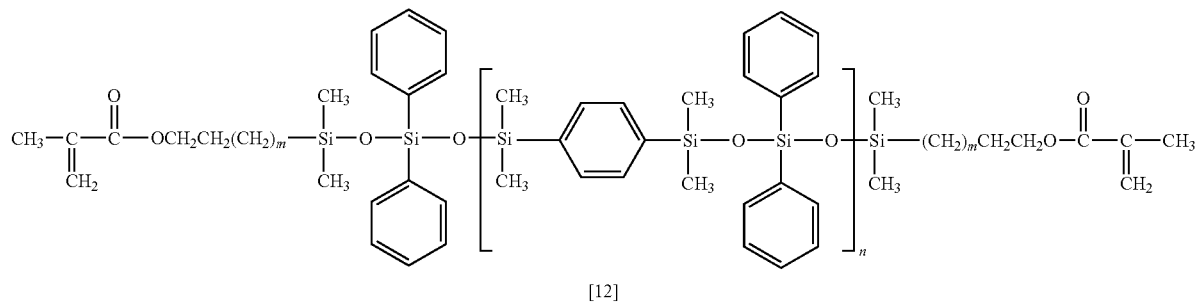

[12]

Reaction 5. Synthesis of Dimethacrylate Terminated Phenylene Siloxane Copolymer [10].

EXAMPLE 3

Representative Copolymeric Materials

| Ingredient | Amount (% w/w) | | | |
|---|---|---|---|---|
| | A | B | C | D |
| Dimethacrylate-terminated polyphenylesiloxane macromonomer [10] | 35.0 | 50.0 | 30.0 | 10.0 |
| PBMA | 49.5 | 0 | 0 | 0 |
| PEA | 0 | 0 | 44.5 | 54.9 |
| PEMA | 0 | 47.2 | 22.7 | 30.0 |
| PEG(1000)DMA | 15.0 | 0 | 0 | 0 |
| EGDMA | 0.5 | 0 | 0 | 0 |
| BDDA | 0 | 1.0 | 1.0 | 3.2 |
| oMTP | 0 | 1.8 | 1.8 | 1.8 |
| N-2-[3-(2'-methylphenylazo)-4-hydroxyphenyl]ethyl methacrylamide | 0 | 0 | 0 | 0.1 |
| Perkadox ® 16S | 1.0 | 1.0 | 1.0 | 1.0 |

PBMA = 4-phenylbutyl methacrylate
PEMA = 2-phenylethyl methacrylate
PEA = 2-phenylethyl acrylate
EGDMA = ethylene glycol dimethacrylate
BDDA = 1,4-butanediol diacrylate
PEG(1000)DMA = polyethylene glycol (1000) dimethacrylate
oMTP = ortho methallyl Tinuvin P This invention has been described by reference to certain preferred embodiments; however, it should be understood that it may be embodied in Is other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A polymeric ophthalmic or otorhinolaryngological device material comprising
   a) a monofunctional acrylate or methacrylate monomer of formula [1];
   b) a difunctional acrylate or methacrylate cross-linking monomer of formula [2], and
   c) a phenylene-siloxane macromer of formula [3a] or [3b]:

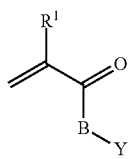
[1]

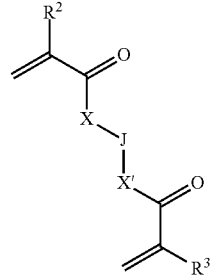
[2]

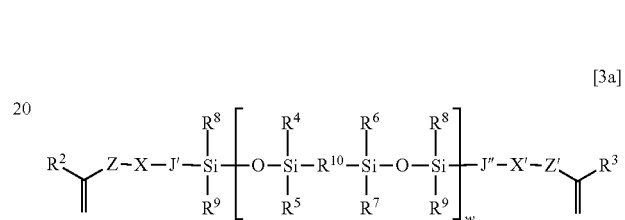
[3a]

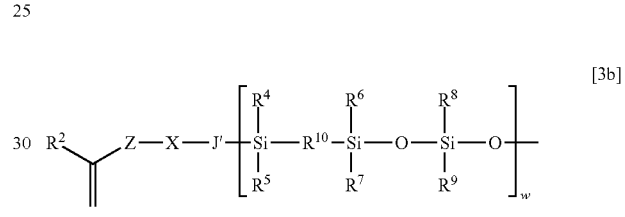
[3b]

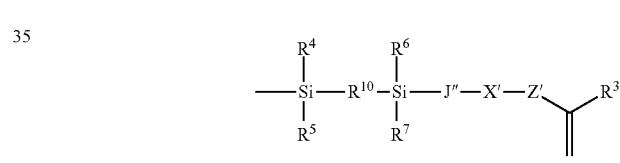

wherein:
B=$O(CH_2)_n$, $NH(CH_2)_n$, or $NCH_3(CH_2)_n$;
$R^1$, $R^2$, $R^3$ independently =H, $CH_3$, $CH_2CH_3$, or $CH_2OH$;
X, X' independently =$O(CH_2)_n$, $NH(CH_2)_n$, $NCH_3(CH_2)_n$, $O(CH_2)_nC_6H_4$, $O(CH_2CH_2O)_nCH_2$, $O(CH_2CH_2CH_2O)_nCH_2$, $O(CH_2CH_2CH_2CH_2O)_nCH_2$, or nothing;
J=$(CH_2)_a$, $O(CH_2CH_2O)_b$, O, or nothing, provided that if X and X'=nothing, then J≠nothing;
J', J" independently =$(CH_2)_a$ or nothing, provided that if X and X'=nothing, then J', J"≠nothing;
n=0-12;
Y=$C_6H_5$, $(CH_2)_mH$, or $O(CH_2)_mC_6H_5$;
Z, Z' independently =C(=O) or $OCH_2C_6H_4$;
m=0-12;
a=1-12;
b=1-24;
$R^4$, $R^5$, $R^6$, $R^7$, $R^8$, $R^9$ independently =$(CH_2)_bH$, $CH=CH_2$, $CH=C(CH_3)$, $CH_2CH=CH_2$, $CH_2CH=CHCH_3$, $CH(CH_3)_2$, $CH_2CH(CH_3)_2$, $O(CH_2)_mC_6H_5$, $O(CH_2)_mC_6H_4(OH)C(O)C_6H_5$, $CH_2CH_2CH_2NH_2$, $CH_2CH_2CH_2NHCH_3$, $CH_2CH_2CH_2N(CH_3)_2$, $CH_2CH_2NHCH_2CH_2NH_2$, $CH_2CH(CH_3)CH_2NHCH_2CH_2NH_2$, $(CH_2)_aOC(O)C(R^1)=CH_2$, $(CH_2)_bSH$, $CH_2CH_2OCH_2C(O)CH_2$, $CH(CH_3)NHCH_2CH_3$, $CH(CH_3)N(CH_3)CH_2CH_3$, CH(CH₃)N(CH₂CH₃)₂, cyclopentyl, cyclohexyl, CH₂CH₂CN, CH₂CH₂CH₂CN, CH₂CH₂CH(CH₃)CN, CH₂Cl, CH₂CH₂Cl, CH₂CH₂CH₂Cl, CH₂CH₂C₆H₄CH₂Cl, CH₂Si(CH₃)₃, CH₂Si(CH₂CH₃)₃, CH₂CH₂CF₃, CH₂NCO, CH₂NHC₆H₅, C₆F₅, phenyl, or naphthyl, each optionally substituted with $C_1$-$C_{12}$ alkyl, $C_1$-$C_{12}$ alkoxy, $C_1$-$C_{12}$ cycloalkyl, $C_1$-$C_{12}$ cycloalkoxy, NO₂, OH, CN, NCO, NH₂, F, Br, Cl, I, or (CH₂CH₂O)$_b$H;

$R^{10}$=phenyl, biphenyl, diphenylether, or naphthyl, each optionally substituted with $C_1$-$C_{12}$ alkyl, $C_1$-$C_{12}$ alkoxy, $C_1$-$C_{12}$ cycloalkyl, $C_1$-$C_{12}$ cycloalkoxy, NO₂, OH, CN, NCO, NH₂, F, Br, Cl, I, or (CH₂CH₂O)$_b$H; and w=3-120.

2. The polymeric ophthalmic or otorhinolaryngological device material of claim 1 wherein in formula [1]

B=O(CH₂)$_n$;
$R^1$=H or CH₃;
n=1-4; and
Y=C₆H₅.

3. The polymeric ophthalmic or otorhinolaryngological device material of claim 1 wherein in formula [2]

$R^2$, $R^3$ independently =H or CH₃;
X, X' independently =O(CH₂)$_n$, O(CH₂)$_n$C₆H₄, or nothing;
J=O(CH₂CH₂O)$_b$ or nothing, provided that if X and X'=nothing, then J≠nothing,
n=0-6; and
b=1-24.

4. The polymeric ophthalmic or otorhinolaryngological device material of claim 1 wherein in formulas [3a] and [3b]

$R^2$, $R^3$ independently =H or CH₃;
$R^4$, $R^5$, $R^6$, $R^7$ independently =CH₃ or CH₂CH₃;
$R^8$, $R^9$ independently =CH₃, phenyl, or naphthyl;
$R^{10}$=phenyl, biphenyl, or naphthyl;
X, X'=O(CH₂)$_n$, O(CH₂CH₂O)$_n$CH₂, O(CH₂CH₂CH₂O)$_n$CH₂, O(CH₂CH₂CH₂CH₂O)$_n$CH₂, or nothing;
J', J''=(CH₂)$_a$;
a=3-12;
Z, Z'=C(=O); and
w=3-90.

5. The polymeric ophthalmic or otorhinolaryngological device material of claim 4 wherein the phenylene-siloxane macromer is a macromer of formula [4a] or [4b]

n=0;
Z, Z'=C(=O); and
w=10-70.

6. The polymeric ophthalmic or otorhinolaryngological device material of claim 3 wherein the monomer of formula [2] is selected from the group consisting of: ethylene glycol dimethacrylate ("EGDMA"); diethylene glycol dimethacrylate; 1,6-hexanediol dimethacrylate; 1,4-butanediol dimethacrylate; poly(ethylene oxide)dimethacrylate (number average molecular weight 200-1000); and their corresponding acrylates.

7. The polymeric ophthalmic or otorhinolaryngological device material of claim 1 comprising 45 to 85% (w/w) of a monomer of formula [1].

8. The polymeric ophthalmic or otorhinolaryngological device material of claim 7 comprising 45 to 75% (w/w) of a monomer of formula [1].

9. The polymeric ophthalmic or otorhinolaryngological device material of claim 1 comprising 1 to 95% (w/w) % of a macromer of formula [3a] or [3b].

10. The polymeric ophthalmic or otorhinolaryngological device material of claim 9 comprising 5 to 70% (w/w) of a macromer of formula [3a] or [3b].

11. The polymeric ophthalmic or otorhinolaryngological device material of claim 9 comprising 10 to 50% (w/w) of a macromer of formula [3a] or [3b].

12. The polymeric ophthalmic or otorhinolaryngological device material of claim 1 comprising one or more ingredients selected from the group consisting of a polymerizable UV absorber and a polymerizable blue-light absorber.

13. The polymeric ophthalmic or otorhinolaryngological device material of claim 12 comprising 0.1 to 5% (w/w) of a polymerizable UV absorber.

14. The polymeric ophthalmic or otorhinolaryngological device material of claim 13 comprising 0.01-0.5% (w/w) of a polymerizable blue-light absorber.

15. The polymeric ophthalmic or otorhinolaryngological device material of claim 1 wherein the device material has a refractive index in the dry state of at least 1.47.

16. An ophthalmic or otorhinolaryngological device comprising the device material of claim 1 wherein the ophthalmic or otorhinolaryngological device is selected from the group

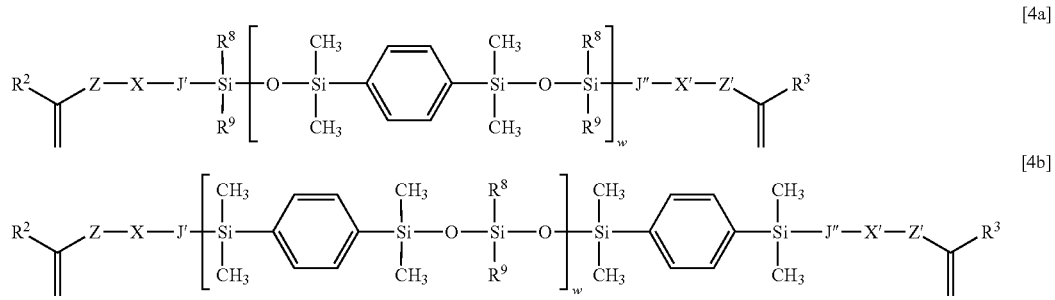

wherein
$R^2$, $R^3$ independently =H or CH₃;
$R^8$, $R^9$ independently =CH₃ or phenyl;
J', J''=(CH₂)$_a$;
a=3;
X, X'=O(CH₂)$_n$;

consisting of intraocular lenses; contact lenses; keratoprostheses; corneal inlays or rings; otological ventilation tubes; and nasal implants.

17. An intraocular lens comprising the device material of claim 1.

* * * * *